(12) United States Patent
Birkenbach et al.

(10) Patent No.: US 10,064,693 B2
(45) Date of Patent: Sep. 4, 2018

(54) CONTROLLING A SURGICAL NAVIGATION SYSTEM

(71) Applicant: Brainlab AG, Munich (DE)

(72) Inventors: Rainer Birkenbach, Erding (DE); Alexander Urban, Forstinning (DE); Alexander Druse, Munich (DE); Axel Besinger, Bad Zwischenahn (DE); Alexander Schaal, Dachau (DE); Till Gerken, Munich (DE); Georg Christian, Munich (DE); Christian Lechner, Jesenwang (DE)

(73) Assignee: Brainlab AG, Munich (DE)

(*) Notice: Subject to any disclaimer, the term of this patent is extended or adjusted under 35 U.S.C. 154(b) by 0 days.

(21) Appl. No.: 15/362,911

(22) Filed: Nov. 29, 2016

(65) Prior Publication Data

US 2017/0071686 A1   Mar. 16, 2017

Related U.S. Application Data

(63) Continuation of application No. 13/519,400, filed as application No. PCT/EP2010/050407 on Jan. 14, 2010, now Pat. No. 9,542,001.

(51) Int. Cl.
*G05B 19/18* (2006.01)
*A61B 34/00* (2016.01)
(Continued)

(52) U.S. Cl.
CPC .............. *A61B 34/74* (2016.02); *A61B 34/20* (2016.02); *A61B 34/25* (2016.02); *A61B 90/39* (2016.02);
(Continued)

(58) Field of Classification Search
None
See application file for complete search history.

(56) References Cited

U.S. PATENT DOCUMENTS

| 4,506,354 A | 3/1985 | Hansen |
| 5,262,807 A | 11/1993 | Shindo |

(Continued)

FOREIGN PATENT DOCUMENTS

| DE | 19639615 A1 | 4/1998 |
| DE | 19845027 A1 | 4/2000 |

(Continued)

OTHER PUBLICATIONS

International Search Report for International Application No. PCT/EP2010/050407 dated Dec. 21, 2010.
(Continued)

*Primary Examiner* — Bhavesh V Amin
(74) *Attorney, Agent, or Firm* — Tucker Ellis LLP

(57) ABSTRACT

Provided is a method for controlling a surgical navigation system. A detection unit for detecting system control inputs made by a user is associated with a surgical navigation system, the navigation system is controlled in accordance with the control inputs, and user gestures are used as said control inputs. A gesture or a initiating user gesture defines a virtual volume surrounding the initiating gesture's limits, and further predetermined gestures made in the virtual volume are recognized as a control input. Also provided is a control system for a surgical navigation system. The navigation system is associated with a detection unit for detecting system control inputs made by a user, the navigation system is controlled in accordance with the control inputs, and the detection unit includes a gesture detection system for detecting user gestures.

17 Claims, 7 Drawing Sheets

(51) Int. Cl.
*G06F 3/01* (2006.01)
*G06F 3/03* (2006.01)
*G06F 3/0346* (2013.01)
*A61B 34/20* (2016.01)
*A61B 90/00* (2016.01)
*G06F 3/0338* (2013.01)
*A61B 17/00* (2006.01)

(52) U.S. Cl.
CPC ............. *G06F 3/014* (2013.01); *G06F 3/017* (2013.01); *G06F 3/0304* (2013.01); *G06F 3/0325* (2013.01); *G06F 3/0338* (2013.01); *G06F 3/0346* (2013.01); *A61B 2017/00115* (2013.01); *A61B 2017/00207* (2013.01); *A61B 2017/00216* (2013.01); *A61B 2034/2048* (2016.02); *A61B 2034/2055* (2016.02); *A61B 2034/2065* (2016.02); *A61B 2034/741* (2016.02); *A61B 2034/742* (2016.02); *A61B 2090/372* (2016.02); *A61B 2090/3937* (2016.02); *A61B 2090/3945* (2016.02)

(56) References Cited

U.S. PATENT DOCUMENTS

| | | |
|---|---|---|
| 5,550,564 A | 8/1996 | Cragun |
| 5,682,886 A | 11/1997 | Delp et al. |
| 5,752,075 A | 5/1998 | Kikinis |
| 5,797,849 A | 8/1998 | Vesely et al. |
| 5,810,008 A | 9/1998 | Dekel et al. |
| 5,825,308 A | 10/1998 | Rosenburg |
| 5,871,018 A | 2/1999 | Delp et al. |
| 5,875,108 A | 2/1999 | Hoffberg et al. |
| 5,988,862 A | 11/1999 | Kacyra et al. |
| 6,031,516 A | 2/2000 | Leiper |
| 6,107,997 A * | 8/2000 | Ure .................. G06F 3/0235 345/156 |
| 6,175,610 B1 * | 1/2001 | Peter .................. A61B 6/00 250/221 |
| 6,219,059 B1 | 4/2001 | Argiro |
| 6,226,548 B1 | 5/2001 | Foley et al. |
| 6,232,891 B1 | 5/2001 | Rosenberg |
| 6,313,853 B1 * | 11/2001 | Lamontagne ......... G06F 9/4443 345/156 |
| 6,359,612 B1 * | 3/2002 | Peter .................. A61B 6/463 345/156 |
| 6,400,996 B1 * | 6/2002 | Hoffberg ............ G05B 19/0426 370/218 |
| 6,433,759 B1 * | 8/2002 | Richardson ........ G02B 27/0093 345/156 |
| 6,462,868 B1 | 10/2002 | Giesberg et al. |
| 6,511,426 B1 * | 1/2003 | Hossack .............. G01S 15/899 600/437 |
| 6,611,252 B1 | 8/2003 | DuFaux |
| 6,720,949 B1 | 4/2004 | Pryor et al. |
| 6,734,880 B2 | 5/2004 | Chang et al. |
| 6,775,577 B2 | 8/2004 | Crnkovich et al. |
| 6,795,068 B1 * | 9/2004 | Marks .................. G06F 3/0304 345/419 |
| 6,931,254 B1 * | 8/2005 | Egner ................ G06Q 30/0269 455/456.1 |
| 6,934,590 B2 * | 8/2005 | Ogawa .................. A61B 6/00 700/19 |
| 6,950,534 B2 | 9/2005 | Cohen et al. |
| 7,030,861 B1 | 4/2006 | Westerman et al. |
| 7,113,193 B2 | 9/2006 | Marks |
| 7,129,927 B2 | 10/2006 | Mattsson |
| 7,136,710 B1 | 11/2006 | Hoffberg et al. |
| 7,158,123 B2 | 1/2007 | Myers et al. |
| 7,317,955 B2 | 1/2008 | McGreevy |
| 7,558,622 B2 | 7/2009 | Tran |
| 7,606,861 B2 | 10/2009 | Killcommons et al. |
| 7,668,340 B2 | 2/2010 | Cohen et al. |
| 7,787,929 B2 | 8/2010 | Kagermeier |
| 7,843,429 B2 | 11/2010 | Pryor |
| 8,155,479 B2 | 4/2012 | Hoffman et al. |
| 8,167,805 B2 | 5/2012 | Emery et al. |
| 8,398,541 B2 | 3/2013 | DiMaio et al. |
| 8,463,006 B2 | 6/2013 | Prokoski |
| 8,538,562 B2 | 9/2013 | Pryor et al. |
| 8,552,983 B2 | 10/2013 | Chiu |
| 8,963,963 B2 | 2/2015 | Hildreth et al. |
| 9,542,001 B2 * | 1/2017 | Birkenbach ............ G06F 3/014 |
| 2001/0030642 A1 | 10/2001 | Sullivan et al. |
| 2001/0049544 A1 | 12/2001 | Lee |
| 2002/0036617 A1 * | 3/2002 | Pryor ...................... G06F 3/042 345/156 |
| 2002/0039084 A1 * | 4/2002 | Yamaguchi ......... G06F 19/3406 345/1.1 |
| 2002/0107573 A1 | 8/2002 | Steinberg |
| 2002/0119990 A1 | 8/2002 | Liu et al. |
| 2002/0145634 A1 | 10/2002 | Gueramy et al. |
| 2002/0183610 A1 | 12/2002 | Foley et al. |
| 2002/0186818 A1 * | 12/2002 | Arnaud .................. A61B 6/563 370/165 |
| 2003/0015632 A1 * | 1/2003 | Dunn .................. A47B 81/065 248/122.1 |
| 2003/0112228 A1 | 6/2003 | Gillespie et al. |
| 2004/0001182 A1 * | 1/2004 | Dyner .................... G09F 19/18 353/28 |
| 2004/0046736 A1 * | 3/2004 | Pryor .................. A63F 13/02 345/156 |
| 2004/0109608 A1 * | 6/2004 | Love ...................... G06K 9/00 382/224 |
| 2004/0161132 A1 * | 8/2004 | Cohen .................. G06F 3/017 382/103 |
| 2004/0193413 A1 | 9/2004 | Wilson et al. |
| 2004/0267695 A1 * | 12/2004 | Alho ...................... G06F 17/50 |
| 2005/0177239 A1 | 8/2005 | Steinberg |
| 2005/0197701 A1 | 9/2005 | Steinberg |
| 2005/0203384 A1 | 9/2005 | Sati et al. |
| 2005/0267353 A1 | 12/2005 | Marquart et al. |
| 2005/0275621 A1 | 12/2005 | Saez et al. |
| 2005/0277832 A1 | 12/2005 | Foley et al. |
| 2005/0285844 A1 | 12/2005 | Morita et al. |
| 2005/0285853 A1 | 12/2005 | Morita et al. |
| 2005/0285854 A1 | 12/2005 | Morita et al. |
| 2005/0289472 A1 | 12/2005 | Morita et al. |
| 2006/0001654 A1 | 1/2006 | Smits |
| 2006/0001656 A1 | 1/2006 | LaViola, Jr. et al. |
| 2006/0009780 A1 | 1/2006 | Foley et al. |
| 2006/0025218 A1 | 2/2006 | Hotta |
| 2006/0026536 A1 | 2/2006 | Hotelling et al. |
| 2006/0033713 A1 | 2/2006 | Pryor |
| 2006/0036944 A1 | 2/2006 | Wilson |
| 2006/0119621 A1 | 6/2006 | Krier |
| 2006/0125803 A1 | 6/2006 | Westerman et al. |
| 2006/0129417 A1 | 6/2006 | Williams et al. |
| 2007/0060247 A1 | 3/2007 | Low et al. |
| 2007/0073133 A1 | 3/2007 | Schoenefeld |
| 2007/0093689 A1 | 4/2007 | Steinberg |
| 2007/0120763 A1 | 5/2007 | De Paepe et al. |
| 2007/0129846 A1 * | 6/2007 | Birkenbach ............ A61B 34/70 700/245 |
| 2009/0027337 A1 | 1/2009 | Hildreth |
| 2009/0183125 A1 | 7/2009 | Magal et al. |
| 2010/0013765 A1 | 1/2010 | Gu et al. |
| 2010/0013812 A1 | 1/2010 | Gu et al. |
| 2010/0053304 A1 | 3/2010 | Underkoffler et al. |
| 2011/0118753 A1 | 5/2011 | Itkowitz et al. |
| 2011/0242305 A1 | 10/2011 | Peterson et al. |
| 2012/0323364 A1 * | 12/2012 | Birkenbach ............ G06F 3/014 700/257 |
| 2013/0245375 A1 | 9/2013 | DiMaio et al. |

FOREIGN PATENT DOCUMENTS

| | | |
|---|---|---|
| DE | 19845030 A1 | 4/2000 |
| DE | 19845028 A1 | 6/2000 |
| DE | 20319951 U1 | 6/2004 |
| DE | 69733265 T2 | 1/2006 |
| DE | 102004049258 A1 | 4/2006 |

(56) References Cited

FOREIGN PATENT DOCUMENTS

| | | |
|---|---|---|
| EP | 1176559 A2 | 1/2002 |
| EP | 1967941 A2 | 9/2008 |
| JP | 1998-063409 A | 6/1998 |
| WO | 0030023 | 5/2000 |
| WO | 2004001569 A2 | 12/2003 |
| WO | 2005092230 A2 | 10/2005 |
| WO | 2006020305 A2 | 2/2006 |

OTHER PUBLICATIONS

Lee et al.;"Using a Mobile Device as an Interface Tool for HMD-based AR Applications"; ACM International Conference Proceeding Series, Proceedings of the 2006 ACM SIGCHI International Conference on Advances in Computer Entertainment Technology, vol. 266; Jun. 14, 2006.

Communication pursuant to Article 94(3) EPC for European Patent Application No. 13170298.7 dated Oct. 14, 2014.

International Search Report for European Patent Application No. 07014276 dated Sep. 19, 2007.

\* cited by examiner

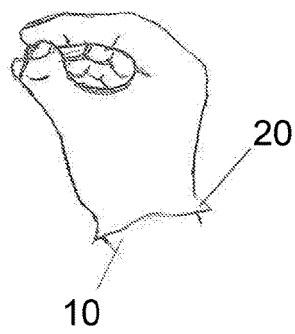
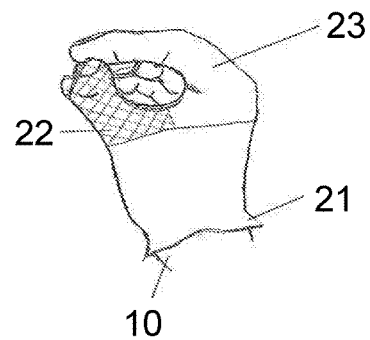
Figure 2
Figure 3
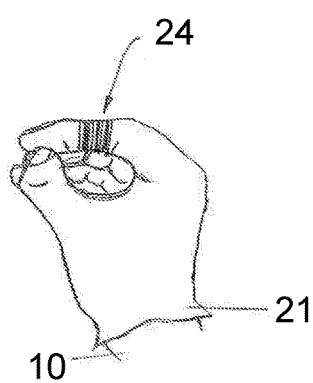
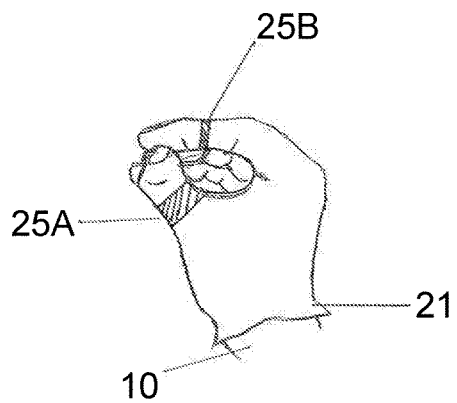
Figure 4
Figure 5

CONTROLLING A SURGICAL NAVIGATION SYSTEM

This application is a continuation of U.S. patent application Ser. No. 13/519,400 filed Jun. 27, 2012 that was a U.S. National Phase of International Application No.: PCT/EP2010/050407 filed Jan. 14, 2010 the entire contents of which are incorporated herein by reference.

The present invention relates to controlling a surgical navigation system. A surgical navigation system is known in general for example from DE 196 39 615 A1, and surgical navigation systems such as the one used in the present invention (for example, image guided surgery systems) are employed in assisting medical personnel in planning and carrying out medical procedures. For example, such navigation systems can be used in association with instrument tracking systems in order to show, on a display, a positional relationship between instruments and a patient's body or part of a patient's body, images of which have been acquired beforehand, for example as CT or MR image data sets. The navigation system can also be used to provide user guidance through a sequence of steps to be carried out during a medical procedure.

When using a surgical navigation system in one of the ways mentioned above or in any other way, there is a need for interaction between the user and the navigation system, for example in order to enter control inputs. Such control inputs can be of various kinds, for example in order to activate a certain procedure or to advance one step in a sequence of navigationally assisted steps in a procedure. Further examples will be referred to below.

Known systems have employed several different means of interaction between a user and a navigation system, including for example touch screens, keyboards and mouses, voice control or remote control. If touch screens are used (in most cases, the screens which are used as the navigation system display), it is necessary to maintain their sterility either by draping them with sterile drapes or by using a sterile touching device such as a sterile pen. Sterile drapes placed over a screen impairs the image quality, in particular when the screen is touched with contaminated hands. Using a sterile pen with a display with no drape allows for good image quality but still incurs a number of general problems. One of these problems is that a user still needs to approach the display in order to interact with the navigation system and may thus be forced to leave their working position. Moreover, such pens are expensive and there is still some risk to sterility, for example if a sterile pen touches an unsterile display or monitor.

The use of keyboards and mouses is rather cumbersome and not intuitive, and there are always problems in providing special keyboards and mouses which can be kept sterile.

The use of voice control is not generally accepted, on the one hand because of the necessity to wear a microphone and on the other hand because of technical problems in identifying spoken commands. Remote controls can be used in sterile bags, but do not generally allow for intuitive control.

It is the object of the present invention to provide a control method for a surgical navigation system which overcomes the disadvantages discussed above. In particular, the invention aims to provide an intuitive way of controlling a navigation system which obstructs the main work of the user, in particular a surgeon, as little as possible, and in particular allows for an unobstructed workflow and/or safeguards the safety of the patient.

To this end, the present invention provides a control method for a surgical navigation system in accordance with claim 1 and a surgical navigation system in accordance with claim 15. The sub-claims define advantageous embodiments of the invention.

The control system for a surgical navigation system in accordance with the present invention is associated with a detection unit for detecting system control inputs, wherein the navigation system is controlled in accordance with such control inputs. The detection unit comprises a gesture detection system for detecting gestures by the user. In the method of the present invention, the navigation system is controlled in accordance with gestures which are used as control inputs.

Using such a "gesture-based" system has several advantages, the main one being that it provides an intuitive remote control method. The user can perform the control gestures at their working location, thus allowing for a fluent working sequence. The sterility of the user is not influenced by controlling the navigation system, because no potentially unsterile input device has to be touched. On the other hand, the gesture control system can operate using gestures which guarantee sterility and others which may involve unsterility, but no further unsterility will be caused by controlling the navigation system in accordance with the present invention. Multiple users can interact with the navigation system via gesture-based inputs.

Moreover, a gesture as mentioned below or particularly a initiating user gesture is used to define a virtual volume surrounding the initiating gesture's limits, and further predetermined gestures made in the virtual volume are then be recognized as a control input. The virtual volume is advantageously defined in the sterile working field of the user.

In one embodiment of the invention, the detection unit is a gesture detection unit comprises a gesture detection system for detecting augmented user gestures. In the method, augmented user gestures are detected by such a gesture detection unit while it performs computer-assisted gesture detection.

For the patient's benefit, the medical environment of the present invention makes it necessary for all interactions and inputs to be very clearly and uniquely recognized and then processed. Merely using hand gestures might make it difficult for the detection unit (for example, a camera system) or the (software-based) gesture detection system to identify whether a certain gesture has been made or to uniquely identify said gesture and its meaning. For this reason, one advantageous embodiment of the present invention envisages augmenting the gestures in such a way that the command given can be easily and reliably identified. Such reliable recognition and unique identification will of course also benefit the patient in terms of the success of the medical procedure. The term "augmented gesture" is for example intended to express that such gestures have a potential to convey information which exceeds that of more usual hand gestures, and it may be said in this respect that in accordance with this aspect of the invention, the gestures are emphasized or made more easily detectable or more unique or more easily differentiated from each other or from other gestures or other hand movements. It may also be said that an information-enhanced or identification-enhanced gesture is one kind of augmented gesture.

In accordance with one embodiment of the invention, the control system can also comprise a gesture support which is moved by the user and designed to augment a user gesture, wherein the gesture detection system is adapted to detect gestures augmented by the gesture support. The term "gesture support" means any device which is capable of supporting or supplementing the user's gesture or any device which can help to better transfer the gesture or its meaning to the gesture detection system. The gesture support can be directly or indirectly attached to the user or a part of the user's body, in particular for example the user's hand or head; it can be a device which is manipulated by the user, in particular a separate or integrated device.

In accordance with the present invention, said gesture support can assume many different forms or embodiments and can feature one or any combination of the following devices or characteristics:

- a glove or part of a glove or strap-on device or clip-on device or ring;
- a sterile, disposable glove or part of a glove or strap-on device or clip-on device or ring;
- a glove or part of a glove or strap-on device or clip-on device or ring, comprising or bearing markings which can be detected by the gesture detection system;
- a glove or part of a glove or strap-on device or clip-on device or ring, comprising or bearing black-and-white or color markings or identifications which in particular identify one or more fingers;
- a glove or part of a glove or strap-on device or clip-on device or ring, comprising or bearing patterns which can be detected by the gesture detection system, such as barcodes;
- an active, in particular light-emitting, or passive, in particular reflective, tracking marker or part of a tracking marker for a marker tracking system associated with the surgical navigation system;
- a medical instrument bearing markings or identifications which can be detected by the gesture detection system;
- an acceleration sensor or gyro-sensor;
- a portable or hand-held support comprising markings and/or identifications such as codes, patterns, coloring or tracking markers which can be detected by the gesture detection system, wherein said support is in particular a hand-held display unit which is separately provided for displaying the markings and identifications, or an instrument which is used in the surgical environment and additionally bears such markings and/or identifications, for example a sterile pen or pointing device.

The above list is not exhaustive but is rather merely intended to show particularly advantageous embodiments of gesture supports which can be used with the present invention. Other devices which can convey the gesture "message" can also be used with the present invention and can be manipulated by the head or hands or arms or other parts of a user's body. For example, it is in general possible to use eye-motion or eye-motion tracking as a gesture or as a way of conveying gestures. Other examples and explanations can be found in the detailed description of embodiments of the present invention below.

The detection unit which performs gesture detection can comprise:

- a camera system for visible light, in particular a video camera system; or
- a camera system for the invisible light spectrum, in particular an infrared camera system; or
- a tracking system such as a time-of-flight camera, a laser scanner, a heat tracking system or heat camera system or a magnetic or electromagnetic tracking system.

According to one further embodiment of the method of the present invention, an initiating user gesture, particularly carried out with a gesture support e.g. a navigated medical instrument which can be detected by the gesture detection system, comprises drawing a certain shape, in particular a geometrical shape (86), which is recognized by the navigation system, whereupon

- a control input is associated with the user gesture, and/or
- an interaction mode is started on the navigation system, in which at least one further user gesture is identified.

Any gesture as mentioned above but particularly the initiating user gesture can be used to define a virtual volume surrounding the initiating gesture's limits, and further predetermined gestures made in the virtual volume can then be recognized as a control input. The virtual volume is advantageously defined in the sterile working field of the user.

In accordance with another aspect of the invention, the gesture support is an elongate navigated medical instrument, and the instrument is moved in the manner of a joystick, the joystick movements being recognized as control inputs. In this connection, the instrument can be of a kind which has a tip and a shaft portion, the joystick movements being made with the tip being fixed and the shaft portion moving. The control inputs can be distinguished by their angle of inclination with respect to a defined virtual plane including the instrument tip, and it is possible to start or define a joystick interaction mode on the navigation system when the instrument enters a predefined region or follows a predefined motion.

In the above described joystick-embodiment, but also in any other embodiments discussed herein, a feedback can be given by the navigation system as to the current interaction or gesture driven control input, in particular

- a visual feedback such as a menu or a highlighted element on a navigation screen, and/or
- an audible feedback such as a confirmation sound.

The invention will now be described in more detail by referring to particular embodiments and to the attached drawings. It should be noted that each of the features of the present invention referred to herein can be implemented separately or in any expedient combination. In the drawings:

FIGS. 2 to 6 show various embodiments of gesture supports comprising a glove;

Figure 1:
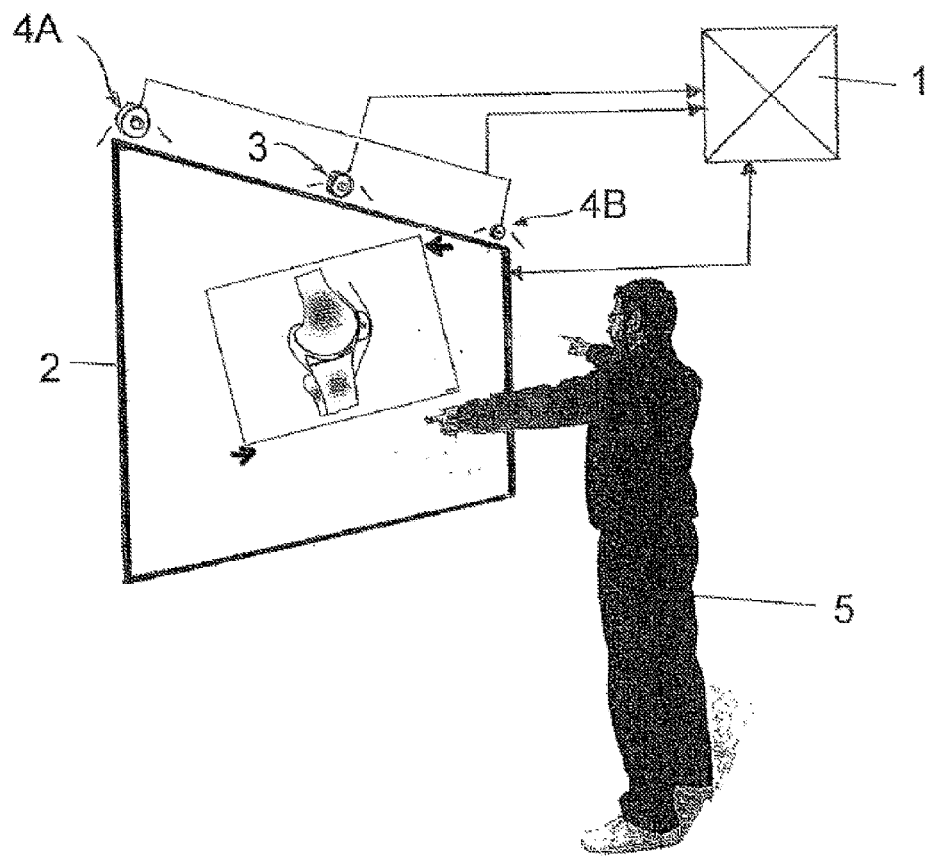
FIG. 1 shows a general embodiment of the present invention in which a user controls a surgical navigation system.

A general embodiment of the present invention is shown in FIG. 1. FIG. 1 shows a user 5 manipulating display items, i.e. images used in medical navigation, which are displayed on a screen 2. The screen can be a monitor or a projection onto a suitable background. It can also be a light box adapted to digitally show and process medical image data.

In the example shown, the user 5 uses freehand gestures to manipulate images on the display 2, for example in order to rotate an image. Rotating an image is shown merely as an example; the user's gestures can perform a variety of commands such as manipulating displayed images or controlling software functions of a medical navigation system. Such a medical navigation system, as a hardware component, is shown in the manner of a black box in FIG. 1. Reference numeral 1 indicates said medical navigation system 1, i.e. its hardware components which include a computer which processes medical image data, displays said data and receives inputs for this purpose. The two-way line connection (double arrow) between the navigation system 1 and the display 2 is intended to show that data is exchanged in both directions between these two hardware components. Some of the hardware of the navigation system can be provided separately or integrated into the display 2.

As mentioned above, the hand gestures by the user 5 are used as control inputs for the navigation system and are detected by a detection unit. FIG. 1 shows two possible embodiments of such a detection unit, one of which is a single video camera 3 which detects the gestures (hand movements) made by the user 5. These gestures are then analyzed by a gesture detection system (software) integrated in the navigation system 1, which converts them into commands. Such commands can be display commands, in which case the navigation system 1 influences the display 2 to adapt the images in accordance with the commands, and/or control commands for the medical navigation system or its software, which are used for example to advance a step further during a navigation-assisted medical procedure.

A number of special gestures can be advantageously used with a system or method according to the present invention. These can include, among other possibilities, the following and/or any combination of them:

| hand movement | outcome |
| --- | --- |
| A cranking or winding movement using one or both hands | To leaf through patient images |
| Bringing both hands or two or more fingers into a predetermined positional relationship | Command to active gesture detection; system then waits for a gesture command |
| Pointing to a certain feature or in a certain direction | To execute a command |
| Moving two fingers away from each other or toward each other | To zoom in/out |
| Pointing to the right/left | Next/previous element (such as an image or command) |
| Thumbs-up | OK |
| Thumbs-down | Cancel |

The assignments mentioned above are of course only some of a variety of possible gestures and associated commands which could be employed in accordance with the present invention.

FIG. 1 also shows a second possible embodiment of a detection unit, namely a two-camera detection system, wherein two cameras 4A and 4B detect gestures made by the user 5 and forward the respective information to the navigation system 1. Using two cameras, it is possible to gather three-dimensional information about the gestures made, which substantially broadens the scope of possible gestures and information inputs. Information about whether a gesture is made near the display or whether elements are performed further away from or nearer to the display can be identified and given a certain meaning in controlling the navigation system. For example, pointing to a spot on the display and then advancing closer to said spot with the finger still pointing could be used to cause the system to zoom-in on a detail in the vicinity of the spot being pointed to.

Although the cameras 3, 4A and 4B can be video cameras which operate in the visible light spectrum, other kinds of optical tracking means can also be used, for example two infrared cameras of a medical tracking system (instrument tracking system) which give excellent 3D information on a tracked object.

The present invention is advantageously performed within the framework of augmented gesture detection, and—as has been mentioned above—implements can be used in the form of gesture supports which help the system to better detect and identify gestures in order to make control more reliable. FIGS. 2 to 12 show examples of the variety of such gesture supports which can be used with the present invention.

The gesture support shown in FIG. 2 is a glove 20 worn on the hand 10 of the user. The glove 20 can simply be a sterile disposable glove such as is commonly used in medical environments, for example in operating theaters. On the other hand, the glove 20 can also exhibit a certain color throughout its fabric, making it more easily detectable or identifiable for the detection system (cameras). Gestures using two hands, each wearing such a glove, can of course also be used within the framework of the control system of the present invention.

The glove 21 shown in FIG. 3 has a marking consisting of two differently colored sections, namely a thumb section 22 exhibiting a darker color and a forefinger section 23 exhibiting a brighter color. In this way, the two sections can be easily detected and separately identified, and their many possible positional relationships with respect to each other added to the variety of possible gestures.

The glove 21 of FIG. 4 has a part of its forefinger section which comprises a marking in the manner of a barcode intended to make said finger and gestures performed using it easy for the control system to identify.

FIG. 5 again shows a glove 21 with two differently colored or patterned sections 25A and 25B on the thumb and forefinger, respectively, enabling gestures which are coded by the positional relationship of the sections 25A and 25B to be made and identified. It is of course also possible to equip other fingers with such markings and for the markings to be at other locations, for example at the fingertips. In any case, the detection units (camera systems) together with their electronics and/or the navigation system can operate in such a way that the detection system is always waiting for a special gesture and automatically identifies such gestures in the images taken.

Figure 6:
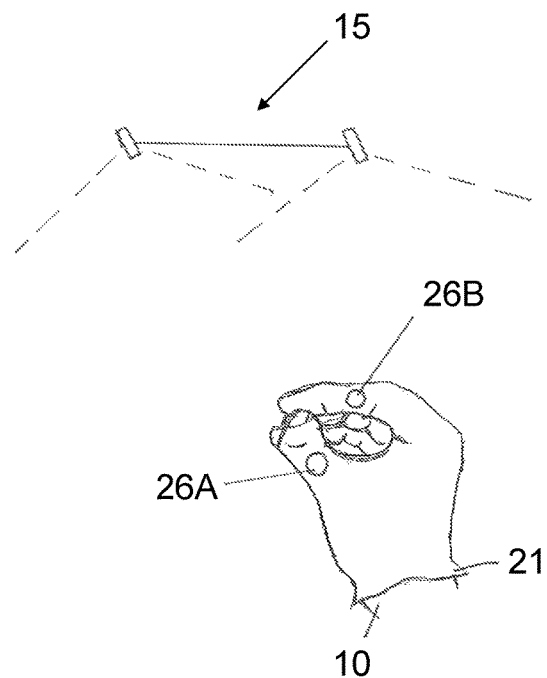

A gesture detection system can also be used which permanently or at certain intervals looks for special markers, an example of which is shown in FIG. 6 in which the thumb and forefinger section of a glove 21 comprise a reflective marker 26A and 26B, respectively, which can be tracked by a medical tracking system which is schematically shown and indicated as 15 in FIG. 6 and comprises two infrared cameras. The markers 26A and 26B can be adhesive and reflective foils, strips or buttons. Very accurate three-dimensional tracking can be carried out by such systems, which are usually capable of tracking medical instruments to accuracies in the order of 1 mm or less. Such tracking makes gesture detection very reliable, and it is advantageously possible to integrate the instrument tracking system and the gesture detection system into a single system, with the instrument tracking camera unit as the gesture detection unit.

In the examples and embodiments of FIGS. 7 to 10, the user's hand is shown bare. It should however be noted that all of these embodiments can of course also be implemented with a user wearing a glove or gloves, in particular sterile disposable gloves for medical purposes. On the other hand, any combination of the embodiments of FIGS. 1 to 12 is conceivable within the framework of the present invention.

Figure 7:
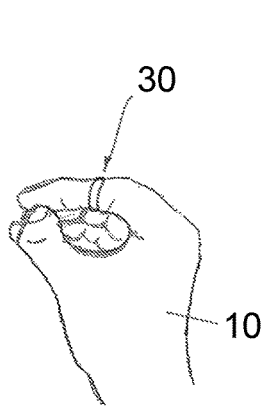
FIG. 7 shows a gesture support comprising a ring.

FIG. 7 shows a ring 30 which is worn on the forefinger of a user's hand 10 and can be a sterile disposable ring which—because of its color, material or markings on it—can be easily identified and detected by the detection unit of the gesture detection system. It is also of course possible to use more than one ring.

Figure 8:
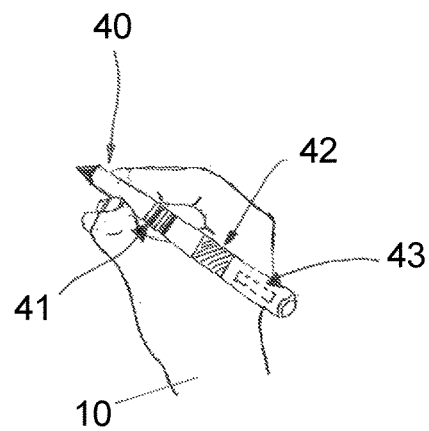
FIG. 8 shows a gesture support embodied as a pen-like device.

FIG. 8 shows an embodiment in which a gesture support is provided as a separate and integrated item, i.e. a hand-held or hand-manipulated item. In the example of FIG. 8, this gesture support is a pen-like instrument, which is ordinarily used for example with a touch screen. The pen 40 as shown in FIG. 8 can be provided with any of the markings discussed herein, and for ease of presentation, three different markings or gesture supports are shown on the pen 40. It is of course also possible for the pen 40 to comprise only one of these, such as a barcode pattern 41, a colored section 42 or an integrated sensor 43, which will be described in more detail below.

In one embodiment of the invention, it is possible to use a sensor such as an acceleration sensor or gyro-sensor as a gesture support. The output of such a gyro-sensor or acceleration sensor can be conveyed wirelessly in a known manner to a receiving unit associated with a medical navigation system. In this way, movements and thus gestures made with the pen 40 would be conveyed or reported to the navigation system as control inputs. In addition to placing a sensor 43 in or on a pen 40, it is also possible to connect such a sensor to any object worn by medical personnel such as a surgeon. The sensor 43 can be integrated into gloves, a mask or any other kind of scrubs. Another possibility would be a small clip which contains such a sensor and can be attached to any part of the surgeon's clothing, since any movements made with the part of the body underneath it would then be indicative of a certain gesture or action. If for example a sensor is arranged on the surgeon's head or on an item worn on the head, a shake of the head can be interpreted as a "No" command, while a nod of the head can be interpreted as a "Yes" command. Any commands already mentioned can be implemented via the acceleration sensor or gyro-sensor, including switching between different views or viewing angles, setting a trajectory or selecting a specific function within the navigation software.

Figure 9:
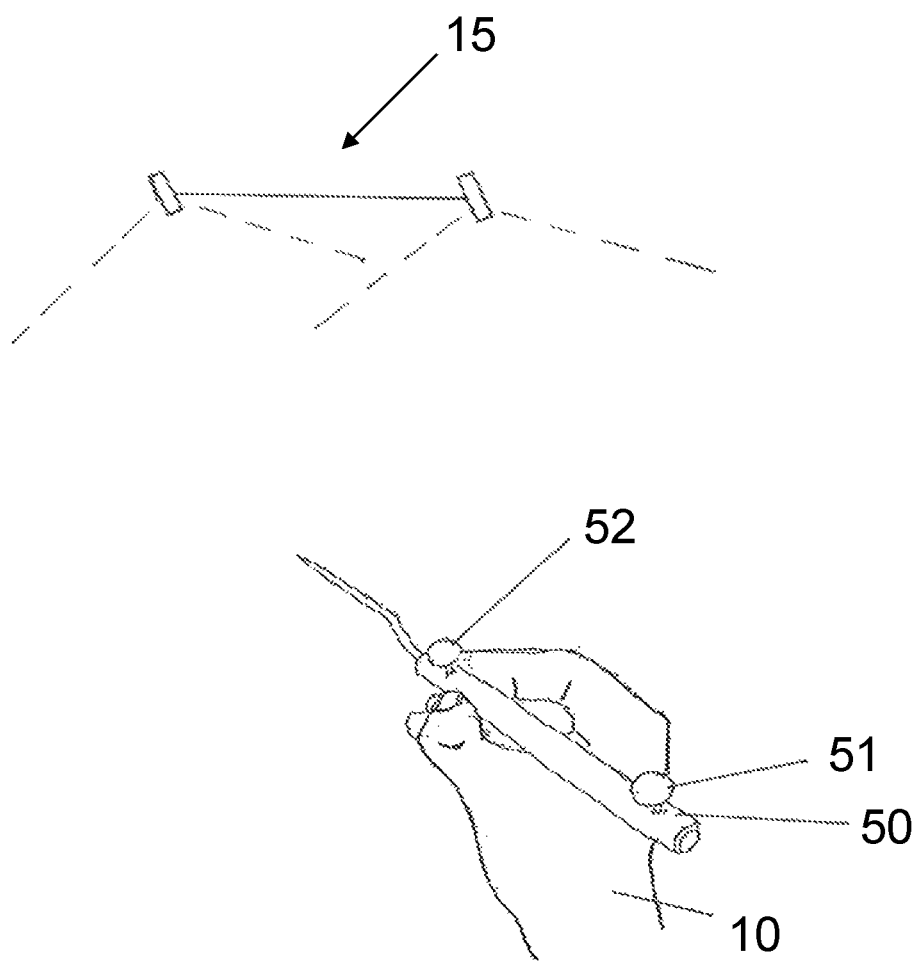
FIG. 9 shows a gesture support embodied as a surgical pointer.

As mentioned above, the instrument tracking system and the gesture detection unit can be integrated, and FIG. 9 shows a pointer 50 comprising reflective markers 51 and 52 which are tracked by a medical tracking system 15 comprising two infrared cameras. Usually, said system is used to very accurately track the tip of the pointer 50, but certain movements performed using the pointer 50 as a gesture support could also of course be interpreted as command gestures. However, these systems need not be integrated in all embodiments of the present invention. It is possible for the markers 51 and 52 to be used on the one hand by the tracking system 15 for position detection and on the other hand for gesture detection by means of a different camera system (not shown) or another capturing mode of the same tracking system 15 (which can for example have an infrared tracking mode and a video capturing mode, integrated in the same unit).

Figure 10:
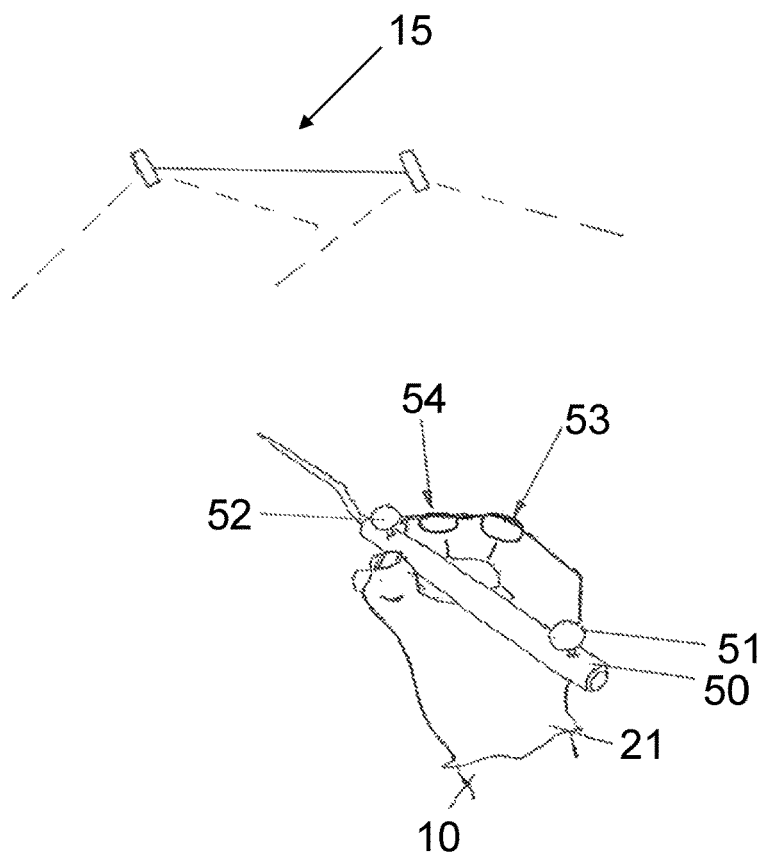
FIG. 10 shows a gesture device composed of a surgical instrument with reference markers and a trackable marker array on a finger of a glove.

Another embodiment, shown in FIG. 10, shows a combination of a tracked instrument 50 comprising a trackable marker array 51, 52 and a trackable marker or marker array 53, 54 on a user's hand 10. Using movements of the trackable marker array 53, 54 (a single marker can be used) relative to the marker array 51, 52, it is for example possible to navigate through the software by identifying certain positions as control input gestures. The markers can be active or passive, i.e. light-emitting or light-reflecting, markers. They can be reflective foils or strips which can be on the side or top of the forefinger or also on the fingertips. The distances or gaps between certain marker elements can be assigned as particular gestures which initialize different commands or functions. This applies to all embodiments described herein which comprise more than one marking on different fingers or objects which can assume variable positions relative to each other. Simple functions such as "accept" or "cancel" can be gestured by movements of the tracked finger relative to the instrument 50; other, more complicated functions can include scrolling up or down a page or setting a trajectory in a navigation environment.

Figures 11, 12:
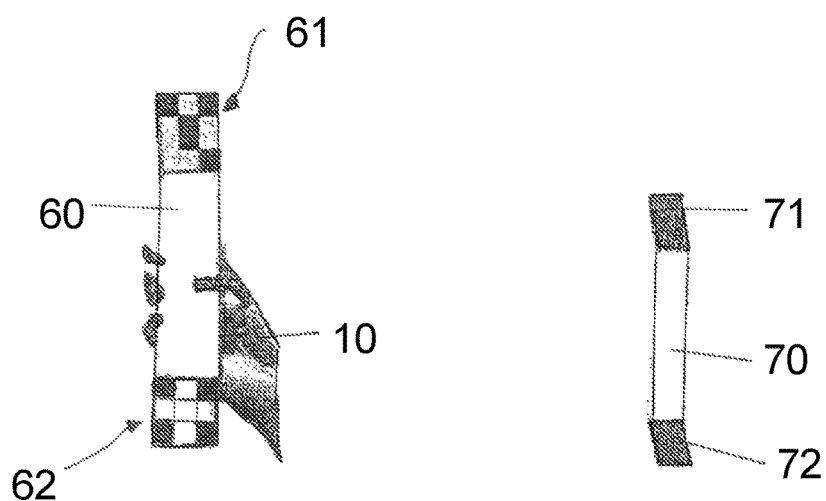
FIG. 11 shows a gesture support with a recognizable pattern.
FIG. 12 shows a gesture support with a recognizable form.

Two other embodiments of gesture supports are shown in FIGS. 11 and 12. These gesture supports can be identified by the detection unit on the one hand on the basis of their color or pattern and on the other hand on the basis of their form. The gesture support 60 of FIG. 11 is an elongated rectangular object which has two different black-and-white patterns 61, 62 on its end sections. Using said patterns 61, 62, complicated gestures can be made and detected and identified, again adding to the variety of possible gestures and therefore input commands for the navigation system control.

FIG. 12 shows a gesture support 70 which is broadly similar to the one in FIG. 11 but less complicated, since the end sections 71 and 72 are merely darker or colored with respect to the middle section. However, the end sections are also bent with respect to the middle section in unique ways which give them a recognizable and distinguishable form for gesture detection, enabling the gesture support 70 to act as another instrument for defining and performing a great variety of accurately distinguishable gestures.

An embodiment of a method according to the present invention will now be explained by means of the drawings in FIG. 13. In this embodiment a user may control the functions of the navigation system by using a navigated instrument within the sterile field above or near the patient.

Figure 13:
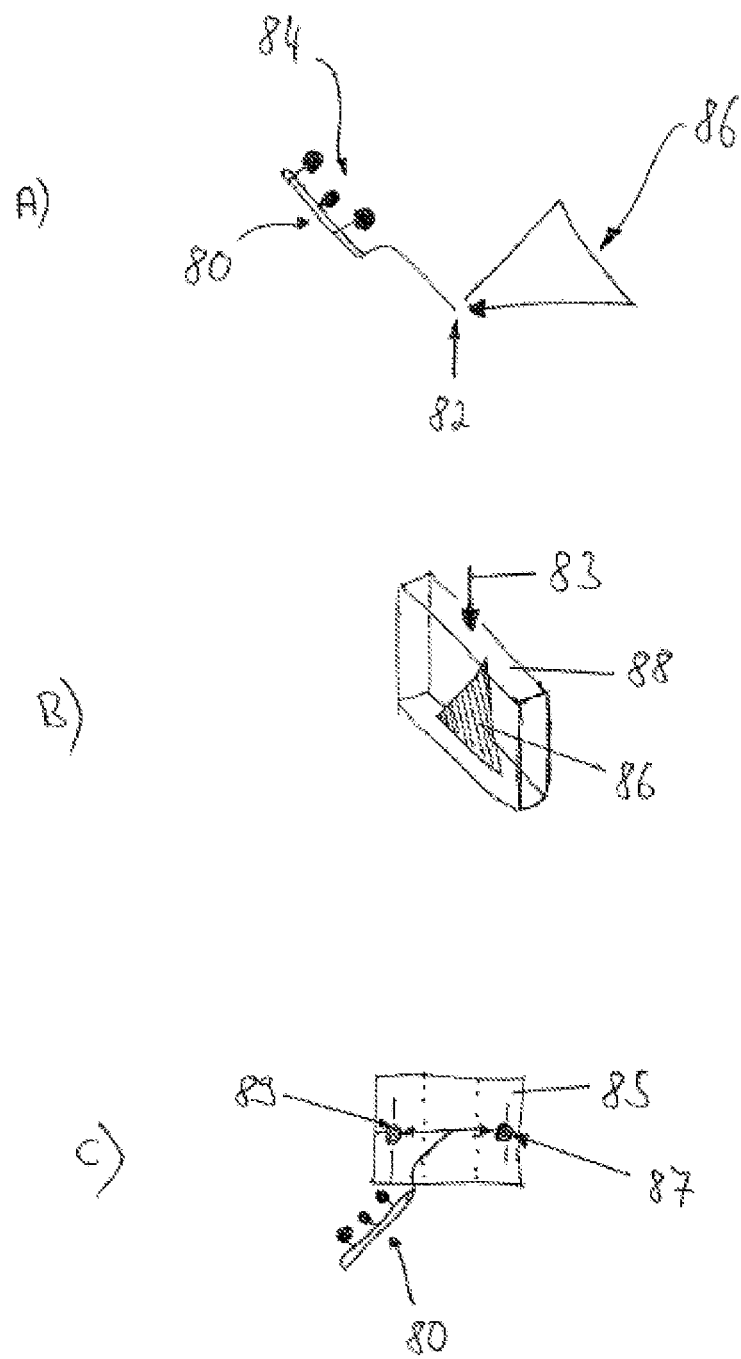
FIG. 13 shows an embodiment of the present invention wherein an initiating user gesture starts an interaction mode.

Part A) of FIG. 13 shows an instrument, namely a pointer 80 having a pointer tip 82 and a reference marker array 84 by which the pointer 80 (including its tip 82) can be located and tracked with the help of a tracking system associated to a navigation system. In order to set up a touch free software control for the navigation system in accordance with the method explained by means of FIG. 13, a user will hold the navigated instrument, i.e. the pointer 80 in his hand. To start the control or interaction mode, the user will draw a geometrical shape like a triangle 86 into the free space next to him within the field of view of the cameras. Of course, the environment can be set up in such a way that the geometrical shape read not be a perfect shape but can be more or less of a geometrical shape such as a triangle, a square or a circle.

In accordance with one possible aspect, this drawing of the geometrical shape is recognized by the navigation system and triggers the software to automatically define a volume of action for controlling the navigation system. Thus, the user does not have to take away his view from the open situs. Moreover, a safe zone for such action may be defined within the sterile field without interference or interruption by instruments, patients, staff, etc. FIG. 13 B) shows an example of such a set-up virtual volume 88 around triangle 86, wherein arrow 83 shows that such a virtual (matrix) volume 88 may also be defined as including a certain direction (for example "down" or "up"). Of course, a certain plane can, e.g., be defined by the geometrical shape drawn.

By means of the initiating user gesture, the navigation system sets up the virtual (matrix) volume around the shape drawn, in which functional instrument movements are located, recognized and interpreted as control movements. As is shown in drawing C) of FIG. 13, once the interaction mode has been entered, the instrument may be used for control purposes or control gestures. A depiction 85 could be shown on a navigation screen, and the movement of the instrument with its tip between two points (89 and 87), although carried out in the sterile field, could be interpreted as a software control command, for example a zoom-command. On the other hand, movements of the instrument can be transferred into the movements of the curser in an x-y direction on the navigation screen, neglecting movements in z-direction.

It is possible to start the control or interaction mode in a different manner. For example, the triggering action could be a "click" or click-like command carried out by means of an active device sending a signal to the navigation system. It could also be a command or "click" on a touch screen button of the navigation system or any other input device like a foot switch. Confirmation or feedback action can be taken, for example the entering of the virtual volume 88 with the tip 82 of pointer 80 could be signalled back by a sound issued by the navigation system. The user could then send a further confirmation by either drawing another geometrical shape or emitting any other signal recognizable by the system as an activation signal or click signal, e.g. by means of an active LED or the like. This avoids any looking away from a point of interest or changing of tools or pressing switches at this time, thus keeping the interruptions for the user at a minimum.

This embodiment provides for the user to keep his view on situs at all times and still have a touch free, intuitive interaction with the navigation system by using the instrument he is handling at that point of time.

Figure 14:
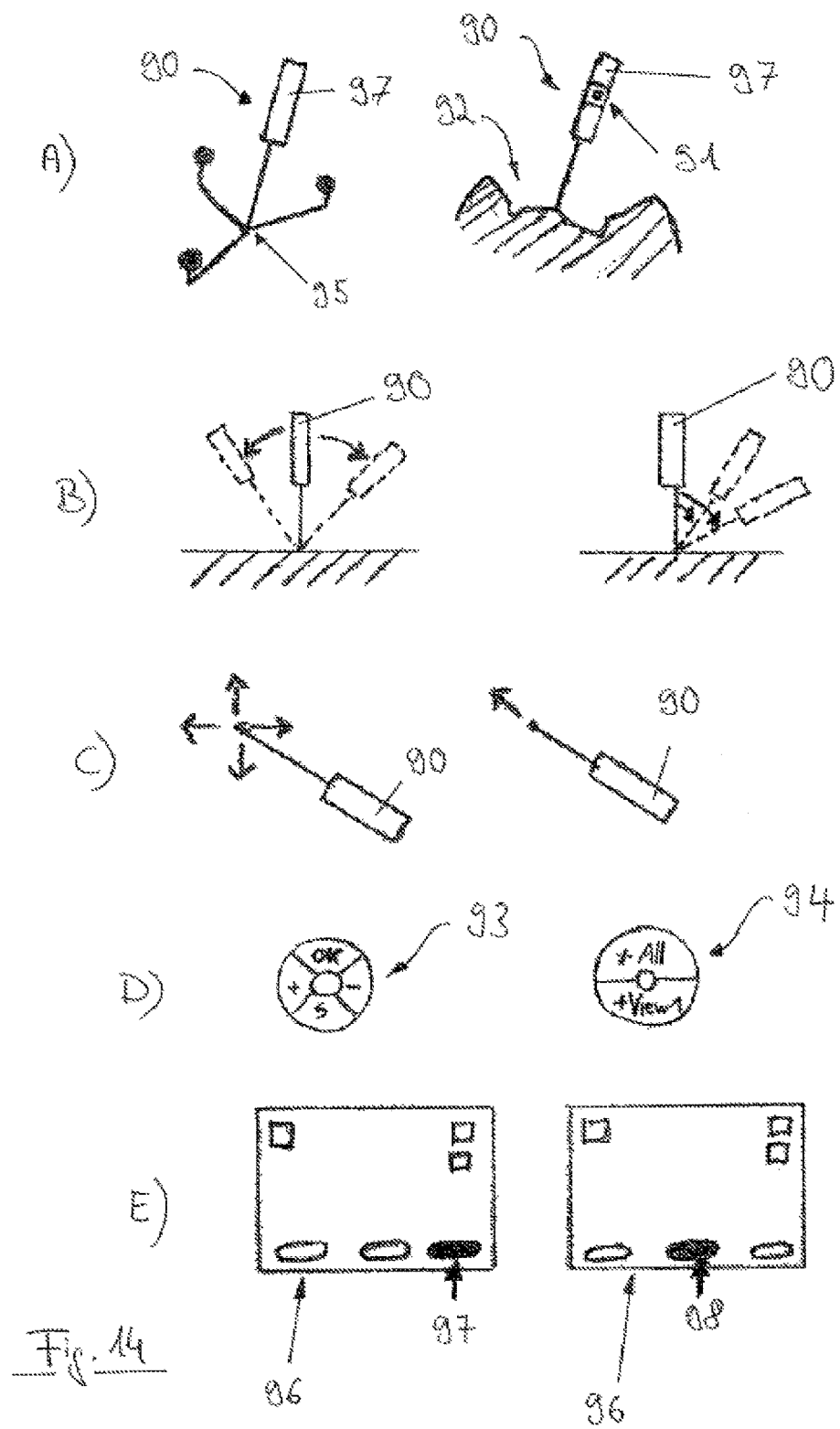
FIG. 14 shows an embodiment of the present invention wherein an instrument is used in the manner of a joy-stick.

In the embodiment shown in the drawings in FIG. 14, the present invention is embodied in such a manner that an instrument is used as a joystick. Thus, the work flow of a medical device, for example, a navigation system, is controlled by a virtual joystick which will provide the user with a well known and intuitive interaction means. The virtual joystick will be simulated by special instrument gestures.

The use of a virtual joystick with a fixed instrument tip is shown in parts A) and B) of FIG. 14. The instrument is a pointer 90 with a shaft 97 and a tip 95, and it may have a signal button 91 to send a signal to a navigation system. The pointer 90 will be located and tracked so that its movements can be followed and interpreted by the navigation system, and the tracking mode can be any known tracking mode as already used in medical navigation, namely magnetic tracking, video tracking or infrared tracking. The tracking mode can be a passive or active tracking mode.

In an interaction mode with a fixed instrument tip as shown in FIGS. 13 A) and B), a first step would consist in activating the joystick mode. As shown in FIG. 14 A) on the left side, the joystick mode can be activated by moving the tip 95 of pointer 90 to a special area or point, for example the pivot point of a reference array of the tracking system (in FIG. 14 A) a reference array with three arms and reflective markers is shown).

On the other hand, the joystick mode could be activated by keeping the instrument still for a certain period of time on any surface 92 (right hand side of A)) or by using a signal button 91 on the instrument.

Once the joystick mode has been activated, the instrument 90 can be used as a joystick by moving its shaft 97. Two properties of the movements can be evaluated, namely one the one hand the direction of the movement like forward, backward, left or right, as is shown in the left hand side drawing of FIG. 14 B). On the other hand, the angle of the movement may also be used as an element of evaluation in translating the movement into a command. The right hand side drawing of FIG. 14B) shows that such a joystick movement can be carried out in a certain angle. One example of such a joystick control scheme would be to move the instrument to the left or the right in order to carry out a zoom-in or zoom-out command (B) left hand side), whereas the angle chosen for this movement defines the zooming speed (B) right hand side, view on left hand side arrangement from the left).

It is possible to accept the chosen action immediately or explicitly by using an additional control element or by keeping the instrument still for a certain period of time. In general, the same actions can be taken as for activating the joystick mode.

While, as described above, joystick gestures may be made with a fixed instrument tip, the instrument may also (or in addition) be used as a free-hand joystick, for example as shown in FIG. 14 C). To this end, the tip of the instrument can be moved in certain predefined directions or the whole instrument can be moved, and those two possibilities may be seen in the left and right hand portions of FIG. 14 C). Again, the workflow control can depend on two properties of the movement, namely direction and, in this case, distance to the center starting point. If the action is to be explicitly acknowledged, the instrument 90 can, for example, be moved forward or along the instrument direction, while a backward movement could be used to cancel an action.

It is possible to make use of an activation region in the working space monitored by the instrument tracking system. That is, depending on the region in which the instrument is located, in particular at the time of switching to the joystick mode, different actions or commands may be possible or recognizable. For example, activating the joystick mode near the patient may trigger a zoom-in/out command for left/right movement, while an activation in other places might lead to interpreting a left/right movement as a "back" or "next" command.

The joystick mode can be used with visual or acoustic feedback given by means of navigation system. For example, when entering the joystick mode, a joystick menu may pop up on the navigation screen showing the current options. Such a joystick menu could be one of those shown in FIG. 14 D), where both menus 93 and 94 are given a circle configuration.

After the joystick mode has been entered, moving the instrument 90 will select or activate the appropriate action. It is also possible to implement sub-menus which are opened when an appropriate menu item has been chosen. For example, choosing the +-side of menu 93 could change menu 93 to menu 94 where the user can select between "zoom-in all views" or "zoom-in only one view".

FIG. 14 E) depicts another possible visual feedback, namely the toggling of buttons on a navigation screen 96. When entering the joystick mode, one button, for example button 97, becomes highlighted. When the instrument is moved, another button, for example button 98 will be highlighted depending on the direction of the movement. The currently selected button can be activated depending on the implemented joystick type, like by moving the joystick forwards, by pressing a button or by keeping the joystick still for a certain time.

Feedback by acoustic signals would, for example, include playing specific sounds when a certain action is selected or activated.

By way of all the implementations and embodiments discussed, the present invention enables the user to work very time-effectively with a medical navigation system, controlling it quickly and without having to be close to the display or to handle less intuitive remote control devices.

The invention claimed is:

1. A method for controlling a surgical navigation system, the method including:
   using user gestures as touch-free system control inputs;
   associating a detection unit for detecting the touch-free system control inputs made by a user with a surgical navigation system;
   controlling the navigation system in accordance with the control inputs;
   moving a medical instrument by the user, wherein predetermined movements of the instrument are detected and identified by the detection unit as user gestures;
   carrying out an initiating user gesture that comprises drawing, with a tip of the medical instrument, a geometrical shape in a free three-dimensional working field of the user above or near a patient;
   recognizing the geometrical shape by the navigation system as the initiating user gesture and defining a virtual volume surrounding the shape drawn in a sterile working field of the user; and
   starting an interaction mode on the navigation system in which at least one further predetermined gestures made in the virtual volume is identified and recognized as a control input.

2. The method according to claim 1, further including:
   moving a gesture support, which is directly or indirectly attached to the user or a part of the user's body and/or which is manipulated by the user, by the user to augment a user gesture; and
   detecting, by a gesture detection unit while it performs computer-assisted gesture detection, augmented user gestures augmented by the gesture support.

3. The method according to claim 2, wherein a gesture support is used which features one or any combination of the following devices or characteristics:
   a glove or part of a glove or strap-on device or clip-on device or ring;
   a sterile, disposable glove or part of a glove or strap-on device or clip-on device or ring;
   a glove or part of a glove or strap-on device or clip-on device or ring, comprising or bearing markings which can be detected by the gesture detection system;
   a glove or part of a glove or strap-on device or clip-on device or ring, comprising or bearing black-and-white or color markings or identifications which identify one or more fingers;
   a glove or part of a glove or strap-on device or clip-on device or ring, comprising or bearing patterns which can be detected by the gesture detection system;
   an active light-emitting or passive reflective tracking marker or part of a tracking marker for a marker tracking system associated with the surgical navigation system;
   a medical instrument bearing markings or identifications which can be detected by the gesture detection system;
   an acceleration sensor or gyro-sensor;
   a portable or hand-held support comprising markings and/or identifications in the form of codes, patterns, colorings or tracking markers which can be detected by the gesture detection system, wherein said support is a hand-held display unit which is separately provided for displaying the markings and identifications or an instrument which is used in the surgical environment and additionally bears such markings and/or identifications.

4. The method according to claim 2, wherein a gesture is made using a combination of a portable gesture support and a marking attached to or associated with the user's hand, and wherein a combined location or movement of the markings on the gesture support and the attached markings constitute the gesture.

5. The method according to claim 1, wherein the gestures are detected by a detection unit comprising:
   a camera system for visible light; and/or
   a camera system for the invisible light spectrum; and/or
   a tracking system in the form of a time-of-flight camera, a laser scanner, a heat tracking system or heat camera system or a magnetic or electromagnetic tracking system.

6. The method according to claim 1, wherein the initiating user gesture, carried out with a gesture support comprises drawing a certain shape, which is recognized by the navigation system, whereupon
   a control input is associated with the user gesture, and/or
   an interaction mode is started on the navigation system, in which at least one further user gesture is identified.

7. The method according to claim 2, wherein the gesture support is an elongate navigated medical instrument, and wherein the instrument is moved in the manner of a joystick, the joystick movements being recognized as control inputs.

8. The method according to claim 7, wherein the instrument has a tip and a shaft portion, the joystick movements being made with the tip being fixed and the shaft portion moving.

9. The method according to claim 7, wherein the control inputs are distinguished by their angle of inclination with respect to a defined virtual plane including the instrument tip.

10. The method according to claim 7, wherein a joystick interaction mode is started or defined on the navigation system when the instrument enters a predefined region or follows a predefined motion.

11. The method according to claim 1, wherein a visual feedback in the form of a menu or a highlighted element on a navigation screen and/or an audible feedback in the form of a confirmation sound is given by the navigation system as to the current interaction or gesture driven control input.

12. A non-transitory computer-readable program storage medium storing a computer program for controlling a surgical navigation system, which, when running on a computer or loaded onto the computer, causes the computer to:
   use user gestures as touch-free system control inputs;
   associate a detection unit for detecting the touch-free system control inputs made by a user with a surgical navigation system;
   control the navigation system in accordance with the control inputs;
   detect and identify, by the detection unit as user gestures, predetermined movements of the instrument when the instrument is moved by the user;

recognize a geometrical shape by the navigation system as an initiating user gesture and define a virtual volume surrounding the shape drawn in a sterile working field of the user, where the initiating user gesture is carried out by drawing, with a tip of the medical instrument, the geometrical shape in a free three-dimensional working field of the user above or near a patient; and start an interaction mode on the navigation system in which at least one further predetermined gestures made in the virtual volume is identified and recognized as a control input.

13. A control system for a surgical navigation system, the control system comprising:

a detection unit associated with the navigation system and configured to detect touch-free system control inputs made by a user and the navigation system configured to be controlled in accordance with the control inputs, the detection unit comprising:

a gesture detection system for detecting user gestures; and a camera system for visible light; and/or a camera system for the invisible light spectrum; and/or a tracking system in the form of a time-of-flight camera, a laser scanner, a heat tracking system or heat camera system or a magnetic or electromagnetic tracking system;

wherein a medical instrument is moved by the user, wherein predetermined movements of the instrument are detected and identified by the detection unit as user gestures, wherein an initiating user gesture is carried out that comprises drawing, with the tip of the medical instrument, a geometrical shape in the free three-dimensional working field of the user above or near a patient, wherein the shape is recognized by the navigation system as the initiating user gesture and defines a virtual volume surrounding the shape drawing in a sterile working field of the user, and wherein an interaction mode is started on the navigation system in which at least one further predetermined gestures made in the virtual volume is identified and recognized as a control input.

14. The control system for a surgical navigation system according to claim 13, wherein the control system further comprises a gesture support which is moved by the user and designed to augment a user gesture, and wherein the gesture detection system is adapted to detect gestures augmented by the gesture support.

15. The control system for a surgical navigation system according to claim 14, wherein the gesture support is directly or indirectly attached to the user or a part of the user's body.

16. The control system for a surgical navigation system according to claim 14, wherein the gesture support is a separate or integrated device which is manipulated by the user.

17. The control system for a surgical navigation system according to claim 15, wherein the gesture support features one or any combination of the following devices or characteristics:

a glove or part of a glove or strap-on device or clip-on device or ring;

a sterile, disposable glove or part of a glove or strap-on device or clip-on device or ring;

a glove or part of a glove or strap-on device or clip-on device or ring, comprising or bearing markings which can be detected by the gesture detection system;

a glove or part of a glove or strap-on device or clip-on device or ring, comprising or bearing black-and-white or color markings or identifications which identify one or more fingers;

a glove or part of a glove or strap-on device or clip-on device or ring, comprising or bearing patterns which can be detected by the gesture detection system;

an active light-emitting or passive reflective tracking marker or part of a tracking marker for a marker tracking system associated with the surgical navigation system;

a medical instrument bearing markings or identifications which can be detected by the gesture detection system;

an acceleration sensor or gyro-sensor;

a portable or hand-held support comprising markings and/or identifications in the form of codes, patterns, colorings or tracking markers which can be detected by the gesture detection system, wherein said support is a hand-held display unit which is separately provided for displaying the markings and identifications or an instrument which is used in the surgical environment and additionally bears such markings and/or identifications.

\* \* \* \* \*